(12) United States Patent
Desilets et al.

(10) Patent No.: US 7,857,773 B2
(45) Date of Patent: Dec. 28, 2010

(54) APPARATUS AND METHODS FOR THE DESTRUCTION OF ADIPOSE TISSUE

(75) Inventors: Charles S. Desilets, Edmonds, WA (US); Cameron Pollock, Sammamish, WA (US)

(73) Assignee: Medicis Technologies Corporation, Bothell, WA (US)

( * ) Notice: Subject to any disclaimer, the term of this patent is extended or adjusted under 35 U.S.C. 154(b) by 1085 days.

(21) Appl. No.: 11/414,080

(22) Filed: Apr. 27, 2006

(65) Prior Publication Data

US 2007/0055156 A1     Mar. 8, 2007

Related U.S. Application Data

(63) Continuation-in-part of application No. 11/026,519, filed on Dec. 29, 2004.

(60) Provisional application No. 60/676,197, filed on Apr. 29, 2005.

(51) Int. Cl.
*A61H 1/00* (2006.01)
(52) U.S. Cl. ............... 601/2; 601/3; 601/4; 606/1; 606/27; 606/28; 606/53; 600/437; 600/439
(58) Field of Classification Search ............ 601/2–4; 606/1, 27, 28, 53
See application file for complete search history.

(56) References Cited

U.S. PATENT DOCUMENTS

| | | |
|---|---|---|
| 3,880,393 A | 4/1975 | Watson |
| 4,002,221 A | 1/1977 | Buchalter |
| 4,059,098 A | 11/1977 | Murdock |
| 4,137,777 A | 2/1979 | Haverl et al. |
| 4,196,630 A | 4/1980 | Rudolph |
| 4,211,949 A | 7/1980 | Brisken et al. |
| 4,291,578 A | 9/1981 | Hetz et al. |
| 4,326,418 A | 4/1982 | Pell, Jr. |
| 4,368,410 A | 1/1983 | Hance et al. |
| 4,421,118 A | 12/1983 | Dow et al. |
| 4,437,033 A | 3/1984 | Diepers |
| 4,444,197 A | 4/1984 | Koyano et al. |

(Continued)

FOREIGN PATENT DOCUMENTS

GB      820814      9/1959

(Continued)

OTHER PUBLICATIONS

Romer Cimcore, "Infinite" [brochure], retrieved from the Internet: < http://www.romer.com/main/index.php> on Nov. 11, 2005, 1 page only.

(Continued)

*Primary Examiner*—Brian Casler
*Assistant Examiner*—Baisakhi Roy
(74) *Attorney, Agent, or Firm*—Townsend and Townsend and Crew LLP

(57) ABSTRACT

Methods and apparatus are described for modifying unwanted tissue for cosmetic reasons. The methods provide a non-invasive manner to perform body contouring by destroying adipose tissue while simultaneously causing collagen contraction in a single procedure so that as destroyed tissue is removed from a treatment volume, the volume shrinks gradually to maintain the skin tone of the treatment area.

11 Claims, 11 Drawing Sheets

U.S. PATENT DOCUMENTS

| | | |
|---|---|---|
| 4,459,854 A | 7/1984 | Richardson et al. |
| 4,501,557 A | 2/1985 | Tamura et al. |
| 4,530,358 A | 7/1985 | Forssmann et al. |
| 4,543,959 A | 10/1985 | Sepponen |
| 4,552,151 A | 11/1985 | Bolomey et al. |
| 4,556,066 A | 12/1985 | Semrow |
| 4,567,895 A | 2/1986 | Putzke |
| 4,593,699 A | 6/1986 | Poncy et al. |
| 4,854,808 A | 8/1989 | Bislach |
| 4,865,042 A | 9/1989 | Umemura et al. |
| 4,901,073 A | 2/1990 | Kibrick |
| 4,932,414 A | 6/1990 | Coleman |
| 4,938,217 A | 7/1990 | Lele |
| 4,960,107 A | 10/1990 | Aida et al. |
| 5,064,340 A | 11/1991 | Genov et al. |
| 5,102,380 A | 4/1992 | Poduje et al. |
| 5,143,063 A | 9/1992 | Fellner |
| 5,195,509 A | 3/1993 | Rentschler et al. |
| 5,219,401 A | 6/1993 | Cathignol et al. |
| 5,259,383 A | 11/1993 | Holstein et al. |
| 5,301,660 A | 4/1994 | Rattner |
| 5,308,222 A | 5/1994 | Bacchi et al. |
| 5,352,301 A | 10/1994 | Panchanathan et al. |
| 5,382,286 A | 1/1995 | Fanning et al. |
| 5,404,387 A | 4/1995 | Hammond et al. |
| 5,419,327 A | 5/1995 | Rohwedder et al. |
| 5,419,761 A | 5/1995 | Narayanan et al. |
| 5,434,208 A | 7/1995 | Batelaan et al. |
| 5,476,438 A | 12/1995 | Edrich et al. |
| 5,477,736 A | 12/1995 | Lorraine |
| 5,505,206 A | 4/1996 | Walloch |
| 5,526,815 A | 6/1996 | Granz et al. |
| 5,568,810 A | 10/1996 | Hamers et al. |
| 5,613,419 A | 3/1997 | Pierson et al. |
| 5,618,275 A | 4/1997 | Bock |
| 5,623,928 A | 4/1997 | Wright et al. |
| 5,626,554 A | 5/1997 | Ryaby et al. |
| 5,669,150 A | 9/1997 | Guertin et al. |
| 5,676,159 A | 10/1997 | Navis |
| 5,695,500 A | 12/1997 | Taylor et al. |
| 5,738,098 A | 4/1998 | Brock-Fisher et al. |
| 5,738,635 A | 4/1998 | Chapelon et al. |
| 5,755,753 A | 5/1998 | Knowlton |
| 5,762,066 A | 6/1998 | Law |
| 5,769,790 A | 6/1998 | Watkins et al. |
| 5,797,849 A | 8/1998 | Vesely et al. |
| 5,816,269 A * | 10/1998 | Mohammed ............... 132/319 |
| 5,820,623 A | 10/1998 | Ng |
| 5,827,204 A | 10/1998 | Grandia et al. |
| 5,852,413 A | 12/1998 | Bacchi et al. |
| 5,871,446 A | 2/1999 | Wilk |
| 5,928,169 A | 7/1999 | Schatzle et al. |
| 5,938,608 A | 8/1999 | Bieger et al. |
| 5,938,922 A | 8/1999 | Fulk, Jr. et al. |
| 6,039,048 A | 3/2000 | Sillberg |
| 6,039,689 A | 3/2000 | Lizzi |
| 6,039,694 A | 3/2000 | Larson et al. |
| 6,071,239 A | 6/2000 | Cribbs et al. |
| 6,085,749 A | 7/2000 | Wardle et al. |
| 6,113,558 A | 9/2000 | Rosenschein et al. |
| 6,126,619 A | 10/2000 | Peterson et al. |
| 6,142,748 A | 11/2000 | Harris et al. |
| 6,152,137 A | 11/2000 | Schwartz et al. |
| 6,217,515 B1 | 4/2001 | Yamakawa et al. |
| 6,233,476 B1 | 5/2001 | Strommer et al. |
| 6,241,753 B1 | 6/2001 | Knowlton |
| 6,261,249 B1 | 7/2001 | Talish et al. |
| 6,264,605 B1 | 7/2001 | Scirica et al. |
| 6,302,848 B1 | 10/2001 | Larson et al. |
| 6,306,146 B1 | 10/2001 | Dinkler |
| 6,309,355 B1 | 10/2001 | Cain et al. |
| 6,312,211 B2 | 11/2001 | Tranchida |
| 6,321,106 B1 | 11/2001 | Lemelson |
| 6,350,245 B1 | 2/2002 | Cimino |
| 6,366,831 B1 | 4/2002 | Raab |
| 6,368,331 B1 | 4/2002 | Front et al. |
| 6,419,648 B1 | 7/2002 | Vitek et al. |
| 6,423,077 B2 | 7/2002 | Carol et al. |
| 6,425,867 B1 | 7/2002 | Vaezy et al. |
| 6,488,639 B1 | 12/2002 | Ribault et al. |
| 6,506,171 B1 | 1/2003 | Vitek et al. |
| 6,507,309 B2 | 1/2003 | McMakin et al. |
| 6,524,250 B1 | 2/2003 | Weber et al. |
| 6,554,826 B1 | 4/2003 | Deardorff |
| 6,561,389 B1 | 5/2003 | Earle |
| 6,575,906 B1 | 6/2003 | Schembri, Jr. et al. |
| 6,595,934 B1 * | 7/2003 | Hissong et al. ............... 601/3 |
| 6,607,498 B2 | 8/2003 | Eshel |
| 6,613,004 B1 | 9/2003 | Vitek et al. |
| 6,618,620 B1 | 9/2003 | Freundlich et al. |
| 6,644,852 B2 | 11/2003 | Crain et al. |
| 6,685,639 B1 | 2/2004 | Wang et al. |
| 6,773,408 B1 | 8/2004 | Acker et al. |
| 6,829,990 B2 * | 12/2004 | Cochran et al. ............ 101/127.1 |
| 6,936,046 B2 * | 8/2005 | Hissong et al. ............... 606/27 |
| 2002/0128592 A1 | 9/2002 | Eshel |
| 2003/0083536 A1 | 5/2003 | Eshel et al. |
| 2003/0171701 A1* | 9/2003 | Babaev ..................... 601/3 |
| 2003/0187431 A1* | 10/2003 | Simonson ................. 606/53 |
| 2003/0212351 A1* | 11/2003 | Hissong et al. ............... 601/2 |
| 2004/0039312 A1 | 2/2004 | Hillstead et al. |
| 2004/0215110 A1 | 10/2004 | Kreindel |
| 2005/0015024 A1 | 1/2005 | Babaev |
| 2005/0043726 A1* | 2/2005 | McHale et al. ............... 606/27 |
| 2005/0055018 A1 | 3/2005 | Kreindel |
| 2005/0154314 A1 | 7/2005 | Quistgaard et al. |
| 2005/0187495 A1 | 8/2005 | Quistgaard et al. |
| 2005/0203490 A1* | 9/2005 | Simonson .................. 606/1 |
| 2005/0228319 A1 | 10/2005 | Kenny |
| 2006/0122509 A1 | 6/2006 | Desilets |
| 2006/0211958 A1 | 9/2006 | Rosenberg et al. |

FOREIGN PATENT DOCUMENTS

| | | |
|---|---|---|
| JP | 06-233776 A | 8/1994 |
| JP | 08-024267 A | 1/1996 |
| JP | 2000-210300 A | 8/2000 |
| JP | 2002-516586 T | 6/2002 |
| WO | WO 98/58588 A1 | 12/1998 |
| WO | WO 00/36982 | 6/2000 |
| WO | WO 02/054018 | 7/2002 |

OTHER PUBLICATIONS

Ayme et al., "Occurance of Transient Cavitation in Pulsed Swatooth Ultrasonic Fields", J. Acoust. Soc. Am. (1988) 84(5):1598-1605.

Clarke et al., "Physical and Chemical Aspects of Ultrasonic Disruption of Cells," J. Acoust. Soc. Am. (1970) 47(2):649-653.

Flynn et al., "A Mechanism for the Generation of Cavitation Maxima by Pulsed Ultrasound," J. Acoust. Soc. Am. (1984) 76(2):505-512.

Fry et al., "Threshold Ultrasonic Dosages for Structural Changes in the Mammalian Brain," J. Acoust. Soc. Am. (1970) 48(6):1413-1417.

Kinney, "Body Contouring with External Ultrasound," Plastic & Reconstruct. Surg. (1999) 103:728-729.

Padmaker, "Thresholds and Mechanisms of Ultrasonic Damage to 'organized' Animal Tissues Symposium on Biological Effects and Characterizations of Ultrasound Sources," (1977) Hazzard et al., Ed., pp. 224-239.

Office Action of Japanese Patent Application No. 2006-547563, mailed Jun. 3, 2010, 4 pages total (English Translation Included).

* cited by examiner

APPARATUS AND METHODS FOR THE DESTRUCTION OF ADIPOSE TISSUE

CROSS-REFERENCES TO RELATED APPLICATIONS

The subject matter of the present application claims priority from Provisional Application 60/676,197 (021356-001220US), filed on Apr. 29, 2005. This application is also a continuation-in-part of application Ser. No. 11/026,519 (021356-001210US), filed Dec. 29, 2004, which claimed the benefit of prior provisional application 60/533,958 (021356-001200US), filed on Dec. 30, 2003. The full disclosures of each of these applications are incorporated herein by reference.

BACKGROUND OF THE INVENTION

1. Field of the Invention

The present invention relates to using ultrasound apparatus and methods for the noninvasive modification of adipose tissue.

2. Description of the Prior Art

Body sculpting has developed into a highly sought after procedure for restoring people to a leaner, trimmer physique. The field of cosmetic surgery has ballooned considerably with developments in both tools and techniques. One of the more popular for quick body sculpting is liposuction.

Liposuction is a method of body contouring that can dramatically improve the shape and contour of different body areas by sculpting and removing unwanted fat. In the United States, more than 400,000 liposuction procedures are performed annually. Recent innovations and advances in the field of liposuction include the tumescent technique and an ultrasonic assisted technique. Traditional liposuction was done by making small incisions in desired locations, then inserting a hollow tube or cannula under the skin in the fat layer. The cannula is connected to a vacuum and the fat is vacuumed out. This procedure indiscriminately removed fat, connective tissue, blood vessels and nerve tissue. The procedure caused bleeding, bruising, trauma, and blood loss; the combination of which restricts the amount of fat that can be removed safely in any given procedure.

The Tumescent technique allows for removal of significantly more fat during the operation with less blood loss. Tumescent liposuction involves injecting saline and adrenalin solution before suctioning. A cannula is again used with a suction device to remove fat. This procedure reduces the bleeding of traditional liposuction. However the procedure still removes a significant amount of non-fat tissue.

A more refined liposuction technique is Ultrasound Assisted Lipoplasty (UAL). UAL is similar to the Tumescent technique, but adds a cannula (or probe) vibrating at ultrasonic frequencies. This vibration disrupts the near volume fat cells and essentially liquefies them for easy removal. UAL uses a low power suction and draws the fat material only in the near vicinity of the cannula tip. This technique is more refined and gentle to the tissue, there is less blood loss, less bruising, less pain, and a significantly faster recovery. All liposuction techniques are invasive and present risks of infection and surgery risks to the patients who under go these procedures.

Furthermore, once the underlying tissue is removed, the skin may become baggy or loose. To combat loose folds of skin or sagging of skin tissue, a patient may elect to have the extra skin removed (by under going a skin excision operation) or elect a skin tightening procedure.

In addition to these invasive forms of liposuction, there are numerous other techniques in the prior art for treating unwanted fat (adipose tissue). These techniques, methods and compositions include, but are not limited to; creams, lotions, garments, massage tools and techniques, therapy procedures involving lasers, RF or ultrasound equipment, general surgery, medication and a host of "home remedies."

Unfortunately none of these procedures provide a one step solution for a patient. The norm is for a patient to undergo multiple treatments, sometimes for the same "trouble spot" on the body, before the patient is satisfied with the results. Techniques and instruments of the prior art are designed for particular applications and operate within parameters specific to one desired outcome.

Thus there remains a need for a single solution to the multiple step problem of either removing or reducing unwanted tissue volume while simultaneously providing for improved cosmetic appearance without the need for secondary or follow on procedures.

There is also a need for a cost effective solution to provide for a simple, quick and effective manner to achieve the desired objective or producing a viable body sculpting procedure in one simple procedure.

BRIEF SUMMARY OF THE INVENTION

Thus it is an objective of the present invention to provide a method and apparatus that can combine the effects of various cosmetic procedures into a single non-invasive procedure that will eliminate or greatly reduce the need for additional procedures.

It is another objective of the present invention to provide a means for controlling the amount of energy needed to treat a problem site depending on the patient and treatment volume.

These and other objectives are achieved through the use of a HIFU ultrasound apparatus and methods for tissue modification.

In a first embodiment there is a method of modifying tissue using high intensity focused ultrasound. The method comprises determining a volume of adipose tissue to be treated, identifying a corresponding surface area of skin over the volume of adipose tissue, moving a HIFU therapy transducer over the surface of the skin and applying therapeutic ultrasound energy into the volume of adipose tissue so that a plurality of cells of tissue necrosis and denatured collagen fibrils are produced.

Alternatively the method may include marking the patient's skin surface to create contour lines and/or guidelines for the HIFU therapy transducer. The motion of the transducer may be continuous or discontinuous. The application of therapy ultrasound energy may be done while the transducer is moving or between segments of movement depending on the desired energy distribution in the volume of adipose tissue. HIFU energy is desirably focused in the volume of adipose tissue to raise the temperature to a level where the adipose tissue is destroyed (or no longer viable) and the collagen fibrils are permanently denatured.

In another embodiment of the present invention, there is an apparatus for the delivery of HIFU energy into a patient. The apparatus having at least one ultrasound transducer adapted for being moved while applying therapy and being capable of depositing an energy flux (EF) greater than 35 J/cm$^2$, typically in the range from 35 J/cm$^2$ to 460 J/cm$^2$, wherein EF is determined by the formula:

$$[(p \times (l/v) \times (dc) \times (nl)]/(sa)$$

wherein p=power,
l=line length,
v=velocity,
dc=duty cycle,
nl=number of lines,
and
sa=scanned area.

Preferably, the apparatus is adapted to deposit sufficient ultrasonic energy to produce an EF value greater than 109 J/cm². Additional embodiments and equivalents will be clear upon a detailed study of the following description.

DETAILED DESCRIPTION OF THE INVENTION

Figure 1:
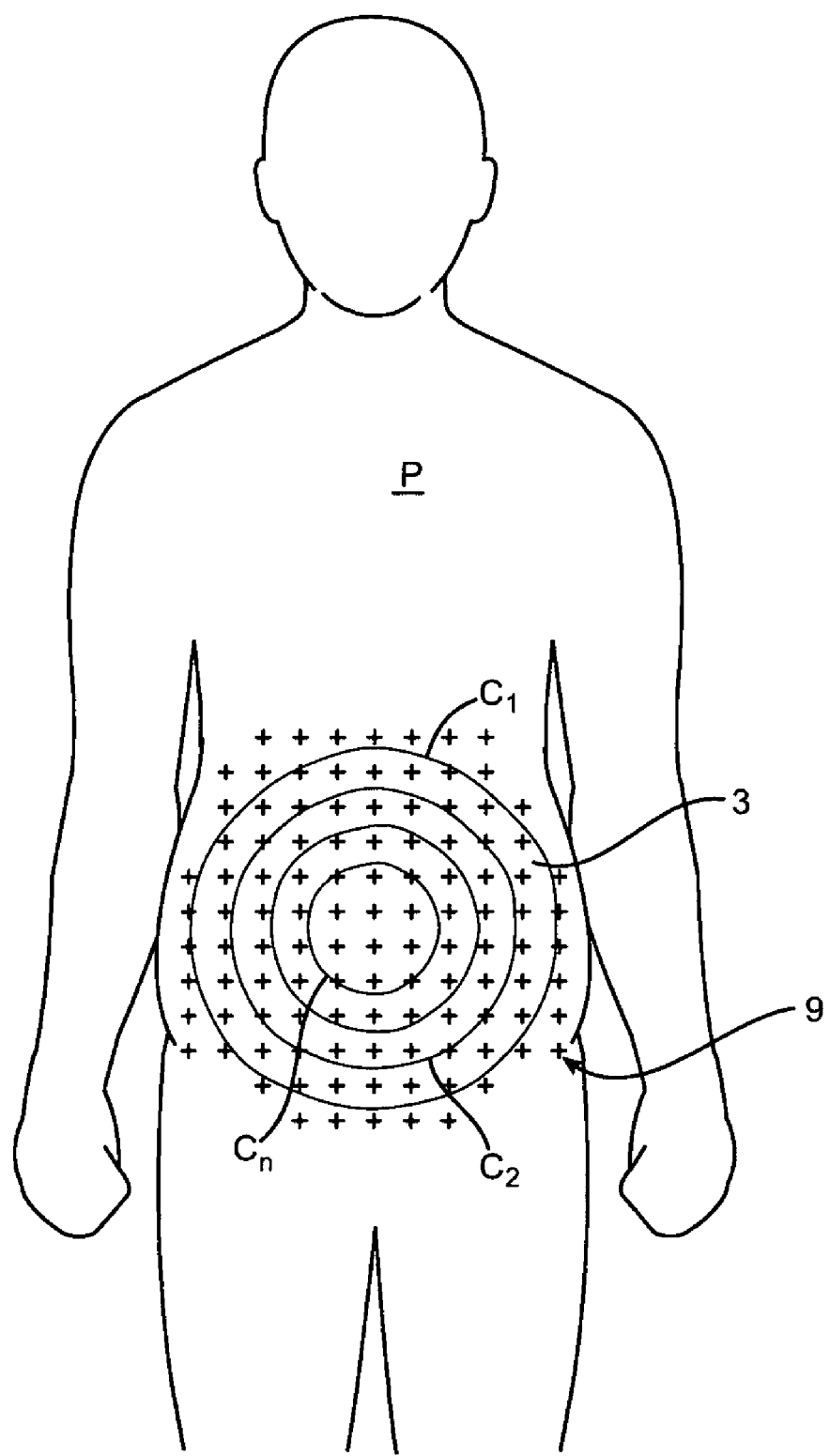
FIG. 1 shows contour and gridlines on a patient.

It should be understood on reviewing the present disclosure that the figures and drawing provided herein are illustrations only. Items shown in these drawings are not intended to be to scale with respect to any key or legend, nor to scale within each drawing. The illustrations may exaggerate particular elements expressly for the purpose of illustrating the element and assisting in the understanding of the accompanying specification.

Methods to address the various issues of patient concern when looking for a non-invasive alternative to liposuction are now described. In one embodiment there is a method of modifying tissue using high intensity focused ultrasound. The method comprises the steps of determining a volume of adipose tissue to be treated, identifying a corresponding surface area of skin over the volume of adipose tissue; and moving a HIFU therapy transducer on the surface area of skin, and applying therapeutic ultrasound energy into the volume of adipose tissue so that a plurality of cells or pockets of tissue necroses and denatured collagen fibrils are produced.

Determining a volume of adipose tissue to be treated is similar to the pretreatment procedures used by cosmetic surgeons prior to a liposuction procedure. A manual pinch test or caliper test can be used by a trained physician to determine if a patient has sufficient adipose tissue at a particular site to warrant a liposuction procedure. The safety measure and standard used by such a test can also satisfy the minimum requirements of a HIFU procedure such as described herein. Alternatively, a physician may use an imaging instrument such as a diagnostic ultrasound device, an MRI device, or a simple A-line scanner to determine if there is sufficient adipose tissue depth in a desired area to be treated using HIFU energy.

While the depth of the adipose tissue should be sufficient to allow the focal zone of the HIFU transducer to be safely in the adipose tissue with some margin of safety both above and below the focal point of the transducer, it should be understood that varying the focal depth of the transducer, as well as the shape and focus of the transducer can allow for more precise control over the delivery of HIFU energy, while simultaneously reducing the clearance zones needed for safe operation. That is to say a highly focused transducer provides sufficient control and focus to allow for a reduced safety clearance.

Once the volume of tissue is identified, the physician should determine the corresponding surface area over the volume that can be treated. Once again, borrowing from existing techniques in liposuction, the physician may proceed directly to treating the patient using a HIFU transducer, or she can create one or more contour lines as part of the treatment planning phase of an ordinary liposuction procedure. During this step the physician may draw or otherwise indicate on a patient skin surface, a region that can safely be treated using a HIFU transducer. Pens or markers may be used to create these contour lines.

Next is the application of HIFU energy into the volume of adipose tissue. A HIFU transducer is moved over the surface area identified above. The transducer emits energy to the focal zone in sufficient strength (power) and intensity (pressure) to cause cellular necrosis and collagen fibril denaturing. Depending on the pulse repetition frequency and velocity that the transducer is moving, a plurality of discrete treatment cells will be produced. Desirably each treatment cell will absorb sufficient energy from the transducer to cause cellular necrosis of all cells in the focal zone, as well as collagen denaturing in the same region. The volume of tissue affected at the focal zone of the transducer is the lesion field 630 (FIG. 3A-5B). The volume around the lesion field 630 where adipose tissue is destroyed and/or collagen fibrils are denatured is the halo field 6. If the transducer is moved in a continuous manner such that a single linear lesion field is formed along the path or axis of motion, the lesion field is said to be contiguous, or a contiguous lesion field 630c. Similarly the halo field 6 may be a contiguous halo field 6c. A volume of over lapping lesion field produced from more than one scan line (such as an intersection) forms a cooperative lesion field, while overlapping halo fields are referred to as cooperative halo fields. Overlapping halo fields may be produced by operating the HIFU transducer in a manner such that scan lines intersect one another, or run parallel close enough so their corresponding halo zones overlap. The sum of the tissue volume of the various lesion fields and halo fields produced during a therapy procedure comprises the treatment area 3.

The destruction of adipose tissue in the lesion field is not restricted to adipocytes (fat cells) alone. The methods described herein are intended to destroy biological tissue within the focal zone by whatever mechanism the HIFU transducer can produce. Furthermore the thermal energy which radiates from the lesion field destroys the surrounding tissue forming the halo field. This thermal radiation is not intended to be of a particular temperature for selective preservation of any biological material. The temperature in the halo field should be sufficient to destroy the adipose tissue and denature the collagen fibrils. Thus, it is likely that other cells or tissue types within the lesion and halo field will be destroyed.

Figure 11:
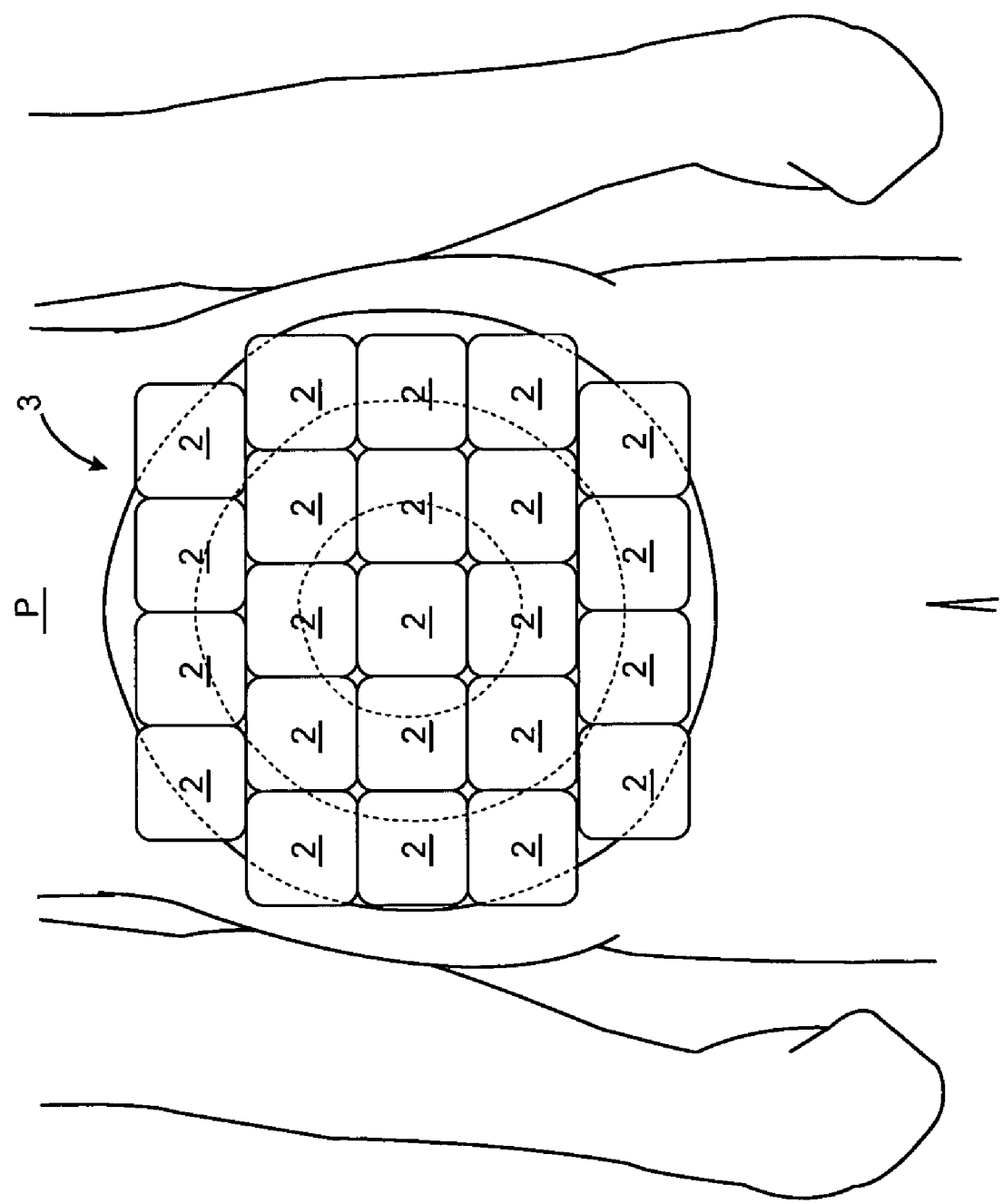
FIG. 11 shows a mosaic of treatment sites used to cover a treatment area.

In one embodiment, the application of HIFU energy may be done in a manner to form a pattern of discrete lesion fields 630 and halo fields 6 within a treatment area 3. In another embodiment, the application of HIFU may be done in a manner that divides the treatment area 3 into a plurality of smaller treatment sites 2, and the sum of the treatment sites 2 produces the desired coverage to form the treatment area 3 (FIG. 11). Alternatively, HIFU energy may be applied in either continuous or discontinuous motion through individual treatment sites 2, or across the entire treatment zone 3. The various treatment sites 2 which form the treatment zone 3 on a patient may be uniform or different in both size of each treatment site 2 within the treatment zone 3, as well as having any mixture of lesion fields 630, contiguous lesion fields 630c, cooperative lesion fields, halo fields 6, contiguous halo fields and cooperative halo fields.

Figure 8:
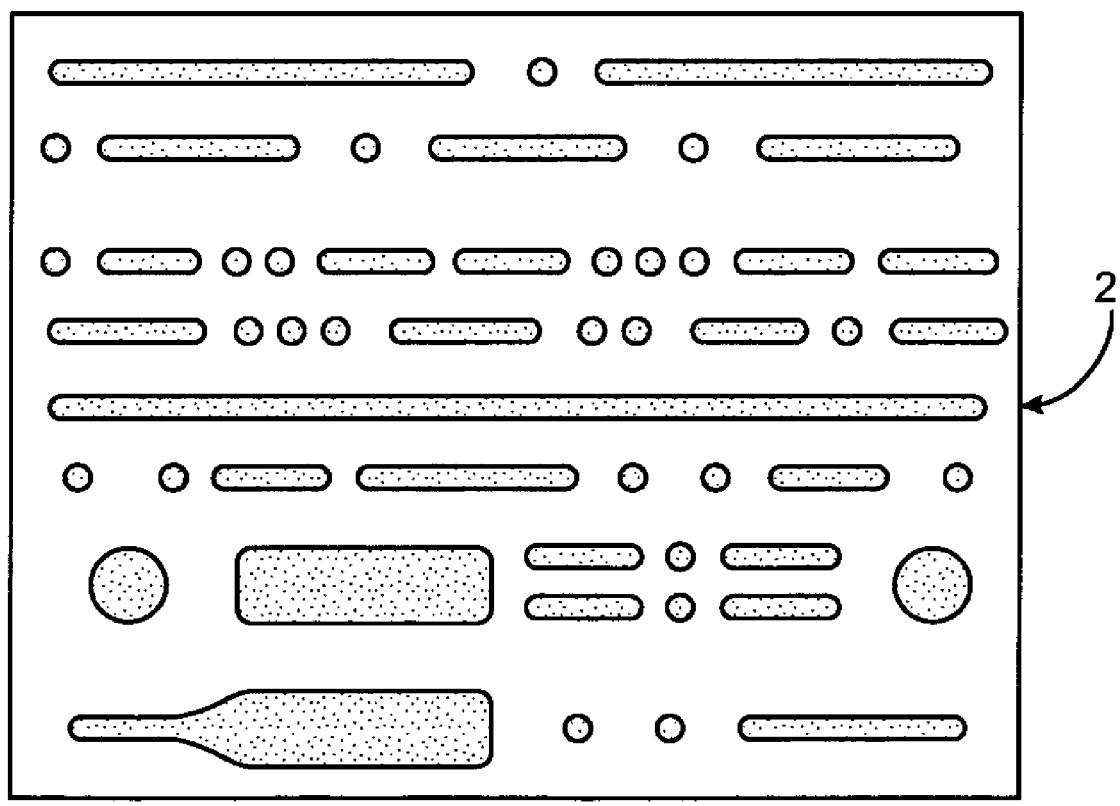

In yet another embodiment of ultrasound application according to the present methods, the transducer may be used to deposit energy and produce lesion fields of varying shapes and sizes. If the transducer is left to reside in a single position (such as using an incremental movement), the transducer may initially create a small lesion field. By allowing the transducer to loiter, thermal energy will build up and radiate out from the lesion field. The transducer may be moved slowly or have higher energy output while moved in a regular movement pattern to produce larger contiguous lesion fields (produce thicker scan lines). By analogy, one may envision the way a fountain pen leaves ink on a page. Just as the nib of a fountain pen allows ink to spread across paper from the point of contact of the nib, so to does thermal energy radiate out from the focal zone of the transducer the longer the transducer is left to loiter over a particular spot of adipose tissue. Some variations of these lesions are shown in FIG. 8. Similar to those scan lines 4, lesion fields 630 and halo field 6 previously described, there are now shown enlarged halo fields. Here the scan line 4 may produce a spot shaped lesion field 630 with a generally spherical shaped halo field 6. Increasing the power broadcast into the tissue may be achieved by moving the transducer slowly, varying the parameters of the transducer, so that more energy radiates from the lesion field into the surrounding tissue, thus producing an enlarged halo field. Similarly, the lesion field itself may also increase in size.

Figure 4A:
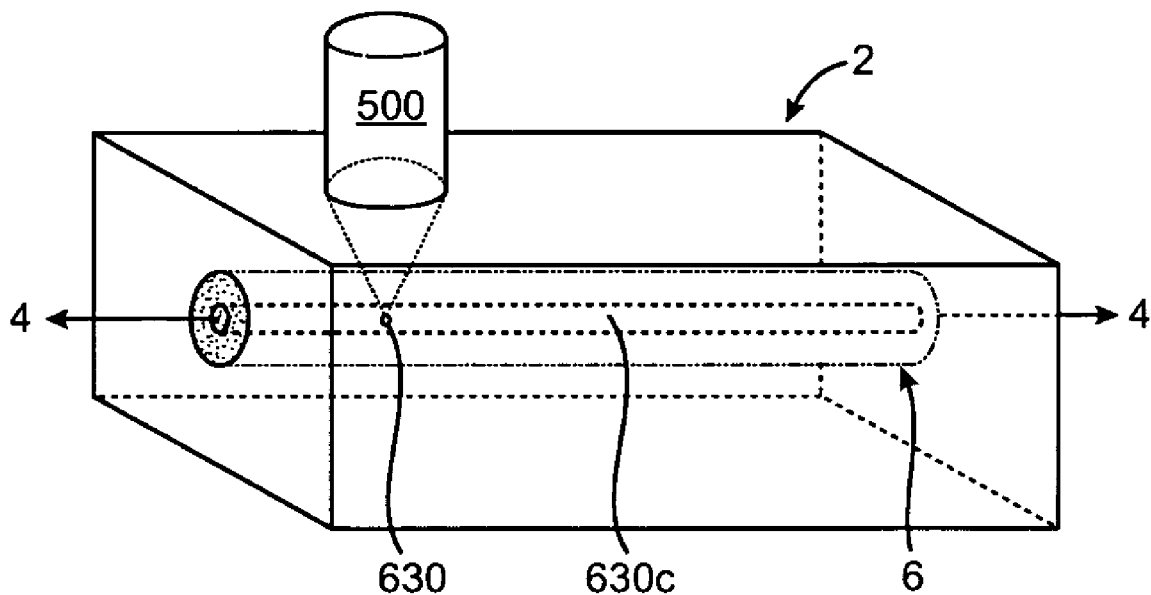
Figure 4B:
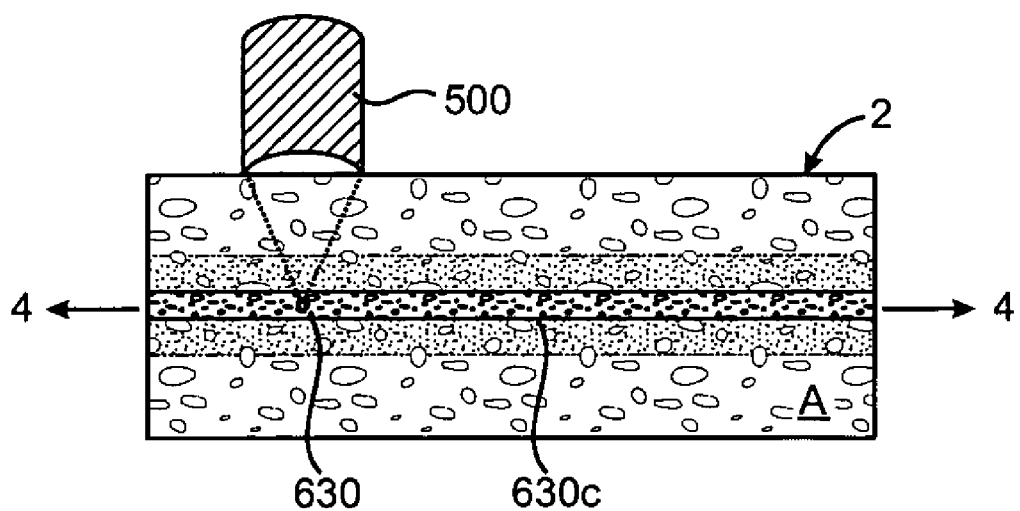

The motion of the transducer over the patient skin can follow any number of patterns. A basic motion is shown in FIG. 4A. Here a transducer 500 is moved in a linear path over the patient skin. The transducer has a focal zone 630 which creates a lesion field. If the transducer is moved in a controlled manner the lesion field formed by the HIFU therapy transducer may form a single, contiguous line of destroyed tissue 630c. The axis of the focal zone in tissue is referred to herein as the scan line 4. Surrounding the scan line 4 is a region of thermal effect desirably raising the local tissue to temperatures sufficient to kill adipose tissue and denature collagen fibrils. This halo field 6 about the scan line 4 represents the volume of tissue which receives sufficient thermal radiation from the lesion field 630, 630c to also be destroyed and denatured. The halo 6 may be large or small depending on how quickly the transducer is moved, and how much power the transducer produces. Here a single scan line 4 is shown within a single treatment site 2 for clarity. A cross section view of a scan line 4 is shown in FIG. 4B.

Figure 3A:
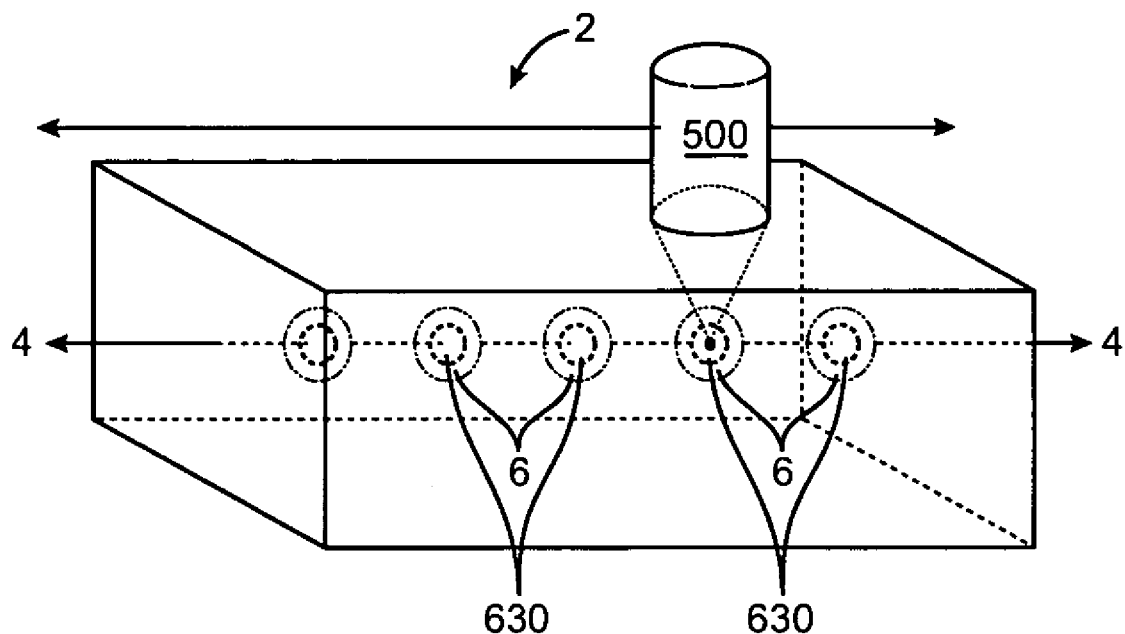
FIGS. 3A-5B illustrate various treatment approaches.
Figure 3B:
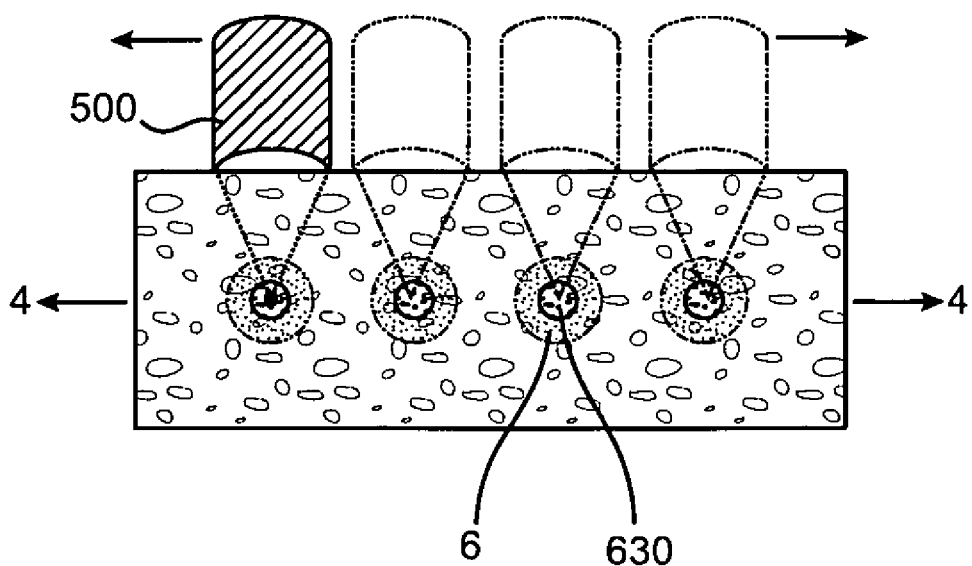

Alternatively, the transducer 500 may be made to produce high intensity pulses or pulse bursts (rapid sequence of discrete pulses) to produce discrete lesions 630 along a scan line 4 (FIG. 3A). In this embodiment, the transducer is desirably moved over the patient skin surface and the transducer is programmed to deliver discrete bursts of HIFU ultrasound energy to produce individual or discrete "cells" of destroyed tissue. The burst of ultrasound energy can produce any variety and number of discrete lesions in the tissue. A halo 6 may also be found surrounding each lesion depending on the operating parameters of the transducer. Again, the pattern of lesion fields and halos are also presented in cross section shown in FIG. 3B.

Figure 5A:
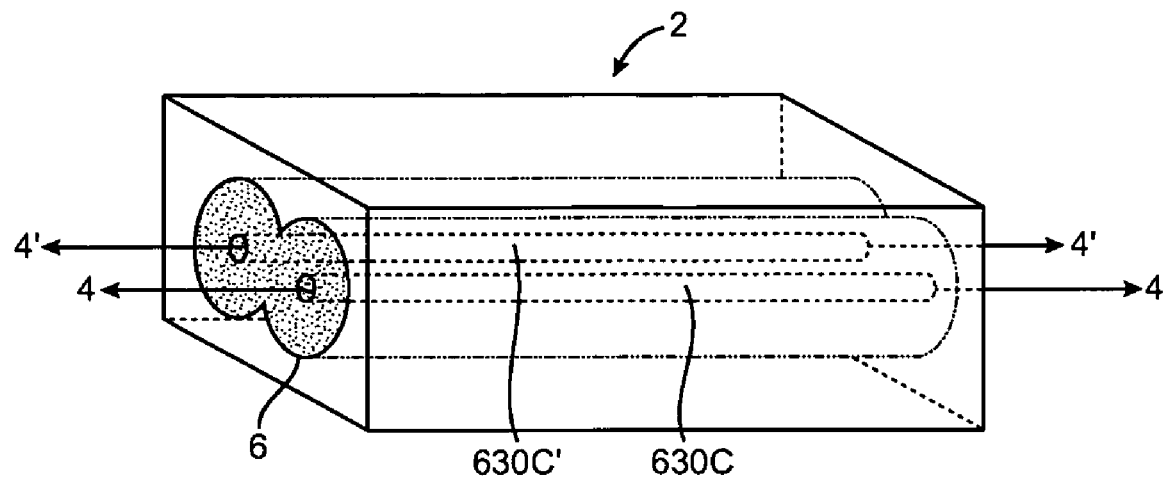
Figure 5B:
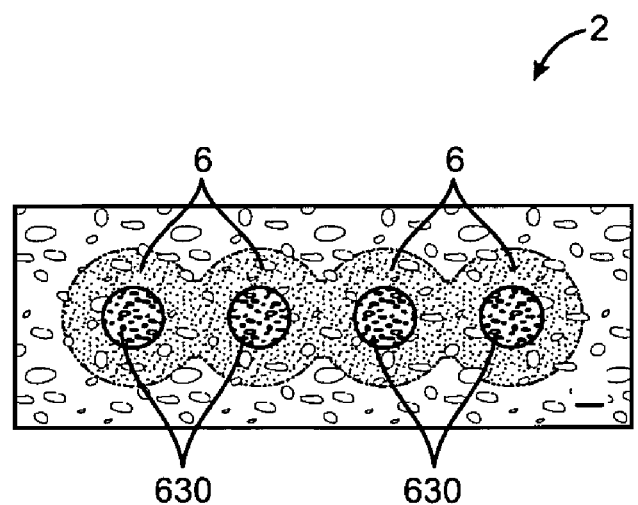

Another embodiment for applying ultrasound energy is illustrated in FIGS. 5A-B. Here two scan lines 4, 4' are shown in close proximity so that the contiguous lesion fields 630c, 630c' are parallel. The halo zone 6 of each scan line run together to form a region of cooperative effect and enlarge the halo zone. Multiple scan lines may be placed side by side to form a large layer of mechanical and thermal effect (FIG. 5B).

Collagen denaturing can occur at temperatures above 37° C. However denatured collagen at temperatures close to normal body temperature may recover, relax and resume their normal length. Desirably then, collagen in the treatment zone is exposed to temperatures above 37° C. More desirably collagen fibrils in the treatment zone are exposed to temperatures above 46° C. and even more preferably to temperatures above 56° C. The higher the temperature the collagen fibrils are exposed to, the shorter the length of time needed to achieve the desired effect (permanent collagen denaturing for contraction of collagen fibrils). When the exposure is at 46° C. the collagen fibrils need to be incubated at that temperature for at least several minutes, however exposure of collagen fibrils to temperatures near or above 56° C. may be done in less than a few seconds. "Collagen Fibril" refers to the collagen material found in adipose tissue or sub dermal regions where collagen concentration tends to be sparse and used by the body as a lattice connective tissue rather than a major structural component (contrast with regions like the nose, ears, skin or tendons and the like). Contraction of collagen fibrils refers to using thermal energy to denature the collagen and force the collagen fibrils to shorten lengthwise.

Desirably adipose tissue is heated using HIFU energy so the temperature in the lesion field is raised as high as practical and as fast as possible. Parameters of the HIFU transducer may be adjusted to produce the desired fast heating needed to destroy adipose tissue and denature collagen fibrils. Desirably the fast heating is balanced with the volume and dimensions of the adipose tissue to be treated. The longer the transducer remains active on one location, the larger the halo field. Desirably the moving of the HIFU transducer and the applying of therapeutic ultrasound energy do not produce lesion or halo fields which extend beyond the dimensions of the adipose tissue volume.

Additional parameters that affect the size of the lesion and halo fields are those parameters electronically controlled through the transducer, and parameters of the transducer itself. These parameters include (but are not limited to) power, frequency, duty cycle, focus, size (of transducer), and pulse repetition frequency.

Figure 6:
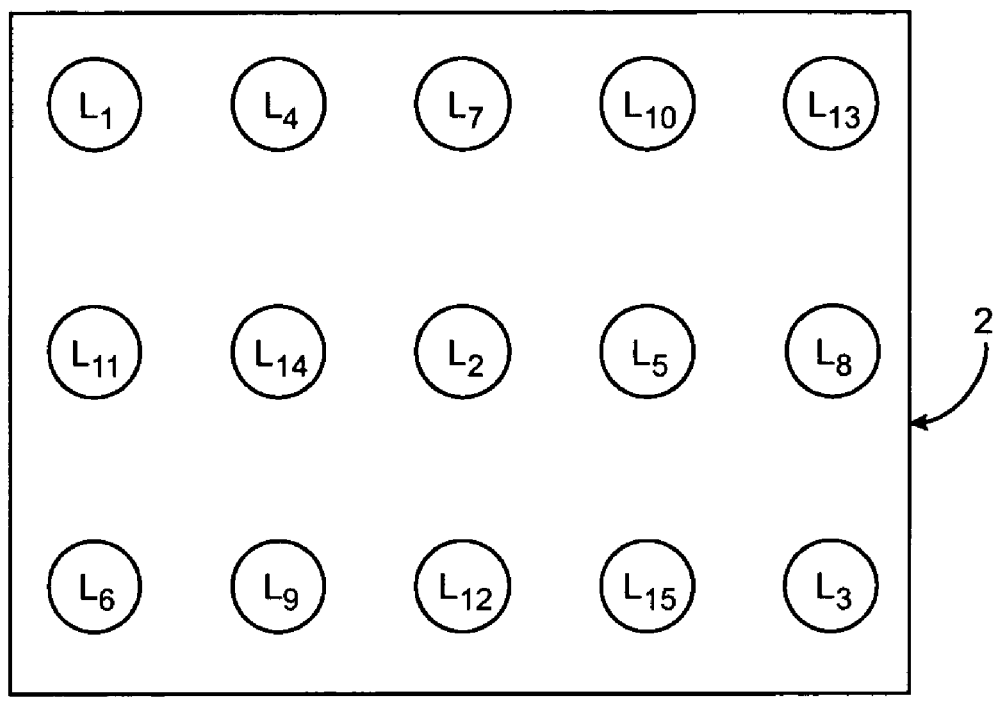
FIGS. 6-8 illustrate various ultrasound treatment patterns.

In some applications, the size of the lesion and halo fields are desirably minimized. This is particularly true where the adipose tissue depth necessitates a tightly controlled lesion and halo field due to proximity of muscle, organs or skin. This can be accomplished by distributing the individual lesion fields within a treatment site apart from each other in both distance and time. If the treatment site is represented by a defined field area 2, then the individual spot lesions may be laid down one at a time in a sequence from $L_1$ to $L_5$ (FIG. 6). Here the lesions are temporally separated as well as being spatially separated. This pattern allows for the individual lesions to have a minimum cooperative thermal effect between lesions. The size of each lesion ($L_{1-n}$) may also be controlled by adjusting the parameters of the ultrasound transducer used in the treatment.

Figure 7:
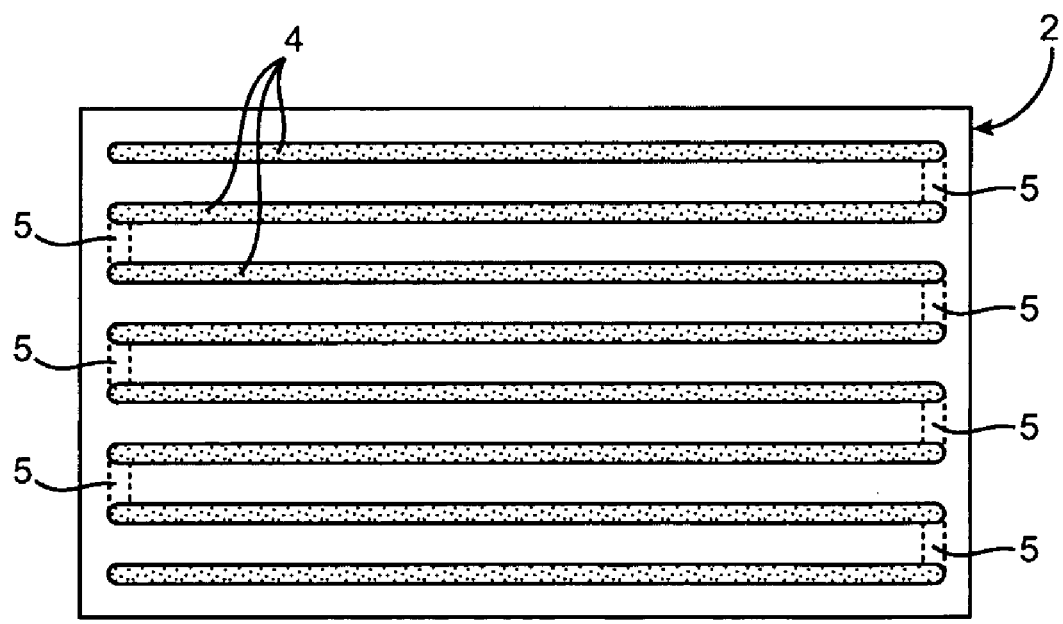

Alternatively, the lesion and halo fields may be maximized by permitting the HIFU transducer to produce contiguous lesion fields and cooperative halo fields. An example of such a maximizing movement scheme is illustrated now in FIG. 7. In this embodiment, the energy required to produce cellular necrosis and collagen contraction is lessened due to the cooperative effect of having the transducer operate in narrowly spaced treatment lines and in rapid succession of laying down treatment lines near each other in both time and space. Movement of the transducer is desirably machine controlled for uniformity and simultaneous control of the transducer. The transducer can treat patient tissue volume by moving over the surface of the tissue volume in any variety of patterns including, but not limited to, spiral, raster scan, or patterned. Thermal cooperation can be maximized by delivering the ultrasound energy as a contiguous lesion field 630 within the treatment site 2. A raster scan type pattern (FIG. 7) may be used with a relatively close line spacing to provide for a maximum of thermal cooperation to produce a large halo region. The horizontal scan lines 4 may be connected with vertical transit lines 5 where the transducer is active, or the vertical transit lines may be "empty" if the transducer is not active while moving vertically. Likewise the spacing between the horizontal lines 4 may be close together or physically overlapping to provide for the maximum overlap of ultrasound energy. Careful planning and consideration in the applying of ultrasound energy in the methods described herein can produce the desired volume of tissue modification in both the amount of adipose tissue destroyed, and collagen denatured.

A balancing of speed (velocity of the focal zone in the tissue being treated) and the power and intensity of the transducer are needed to produce the desired effect. A method of determining the various parameters to use in a tissue modification is now described. In this embodiment, there is a method of reducing adipose tissue volume in a patient using high intensity focused ultrasound. The method comprises the steps of determining a volume of adipose tissue to be treated; marking out a corresponding surface area of skin and applying high intensity focused ultrasound energy to said area in a manner sufficient to induce the gradual destruction of said adipose tissue and denaturing of collagen fibrils, the energy flux being of at least than 35 J/cm². Operationally the speed of destruction may be quickened by providing higher EF values. By scanning the transducer over a volume of adipose tissue at higher EF values, the amount of time needed to achieve adipose tissue necrosis and collagen fibril denaturing can be reduced. Using EF values between 90 and 225 Joules per square centimeter allow for the desired treatment to be done quickly. Further increasing the EF to higher values also produces viable results under certain conditions, going as high as 460 J/cm².

By using a predetermined energy flux value, the transducer can be programmed to consistently and accurately deposit the same amount of energy into each of the lesion fields (also referred to as the focal zone). Through experimentation and analysis, we have found that tissue ablation of adipose tissue and collagen contraction can occur at energy fluxes above 35 joules per square centimeter. Variations in desired outcomes and tissue variations from patient to patient make calling out an exact energy flux figure impossible. However empirical data from multiple study sources suggest the energy flux value should be greater than 35 joules per square centimeter and are probably most efficacious for the dual purpose of destroying adipose tissue and denaturing collagen fibrils at or above 109 joules per square centimeter.

In a physical embodiment of the present invention, there is an apparatus for the delivery of therapeutic ultrasound energy into a patient. The apparatus having at least one ultrasound transducer adapted for being moved while applying therapy and being capable of depositing an energy flux (EF) greater than 35 J/cm², wherein EF is determined by the formula:

$$[(p) \times (l/v) \times (dc) \times (nl)]/(sa)$$

wherein
p=power,
l=line length,
v=velocity,
dc=duty cycle,
nl=number of lines
and
sa=scanned area.

The formulation provided provides for a calculation when the transducer is moving continuously while applying ultrasound energy. Alternatively for a treatment program where the transducer is not moving between therapy applications, the EF can be calculated using the following modified EF equation.

$$EF=[(p) \times (t) \times (dc) \times (ns)]/(sa)$$

wherein
p=power,
t=on-time per lesion,
dc=duty cycle,
ns=number of lesions,
and
sa=scanned area.

Variations in the formula can be derived by those skilled in the art to determine the proper calculations for a therapy program having a mixed set of moving and non-moving treatment sites. The therapy controller desirably allows for a wide variation in parameters which a user may manually feed into the therapy controller prior to each application of ultrasound. The therapy controller determines which variables are to be used and weights them accordingly. An example of a medical instrument system for use with the methods described herein is further described in co-pending U.S. patent application Ser. No. 11/027,912 entitled "Ultrasound Therapy Head with Movement Control" the contents of which are herein incorporated by reference.

Another example is described in co-pending U.S. patent application Ser. No. 11/026,519 entitled "Systems and Methods for the Destruction of Adipose Tissue" filed on Dec. 29, 2004, the contents of which are herein incorporated by reference. The apparatus for the delivery of therapeutic ultrasound energy into a patient has a scan head, suspension device for supporting the scan head, and a therapy controller. The therapy controller is adapted to monitor the position and energy deliver of the scan head.

The various parameters of the Energy Flux equation can be programmed into the therapy controller. The apparatus may have some parameter data programmed in fixed memory and not adjustable by the user. Some elements may include maximum and minimum settings of the transducer to prevent the apparatus from being operated in an unsafe manner.

A user can provide variables into the system to help the system determine the proper EF to be used during a procedure. For example if the user wishes to increase cooperative heating between scan lines, the scan lines (nl) may be set to a higher value. Alternatively the velocity may be reduced to promote larger halo fields, or the velocity may be increased to decrease halo fields as might be required for regions of adipose tissue which have smaller margins.

Figure 9:
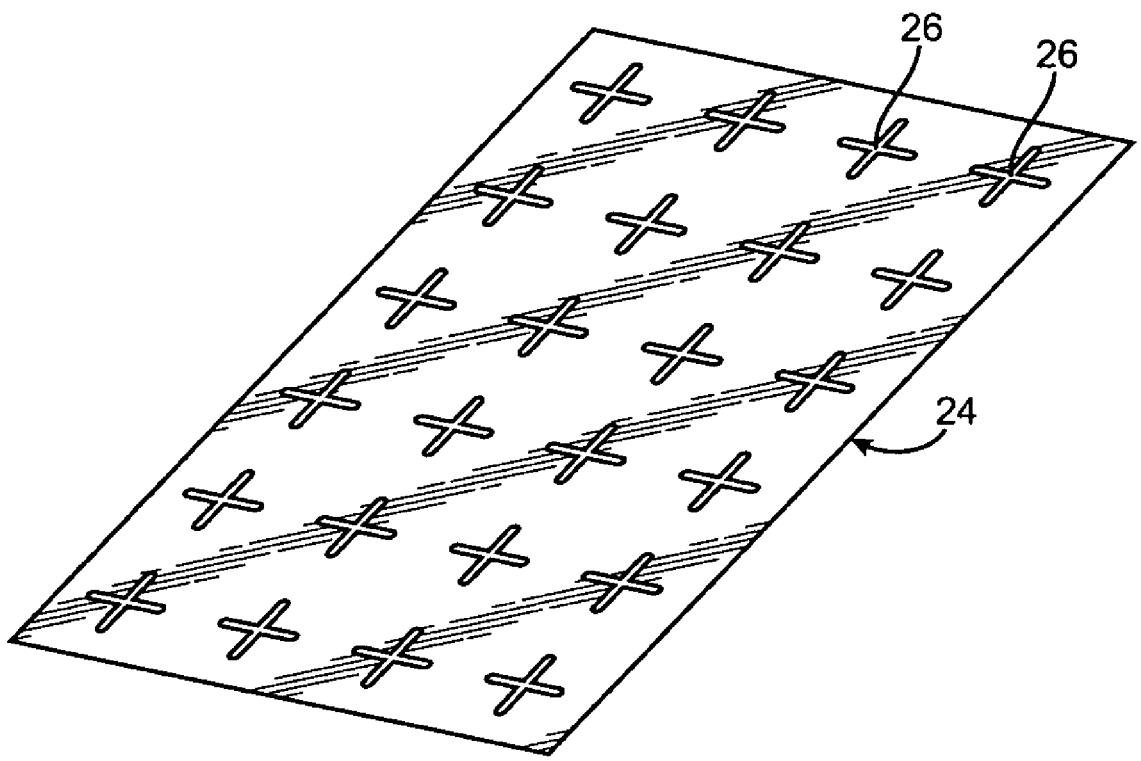
FIG. 9 illustrates a stencil.

A stencil or template 24 can be used to assist a physician in planning the treatment (FIG. 9). The template 24 has a series of apertures 26 in the form of "crosshairs" which can be used to guide the ultrasound transducer during the treatment procedure. The template 24 desirably is created so the apertures match the foot print of the transducer to be used (or therapy device depending on the ultrasound system selected). The template may be used across the skin prior to the creation of contour lines or prior even to the evaluation of the adipose tissue in the target region. Desirably a physician will mark the contour lines and crosshair marks after making the determination of suitable adipose tissue depth in the patients target treatment region.

Figure 2:
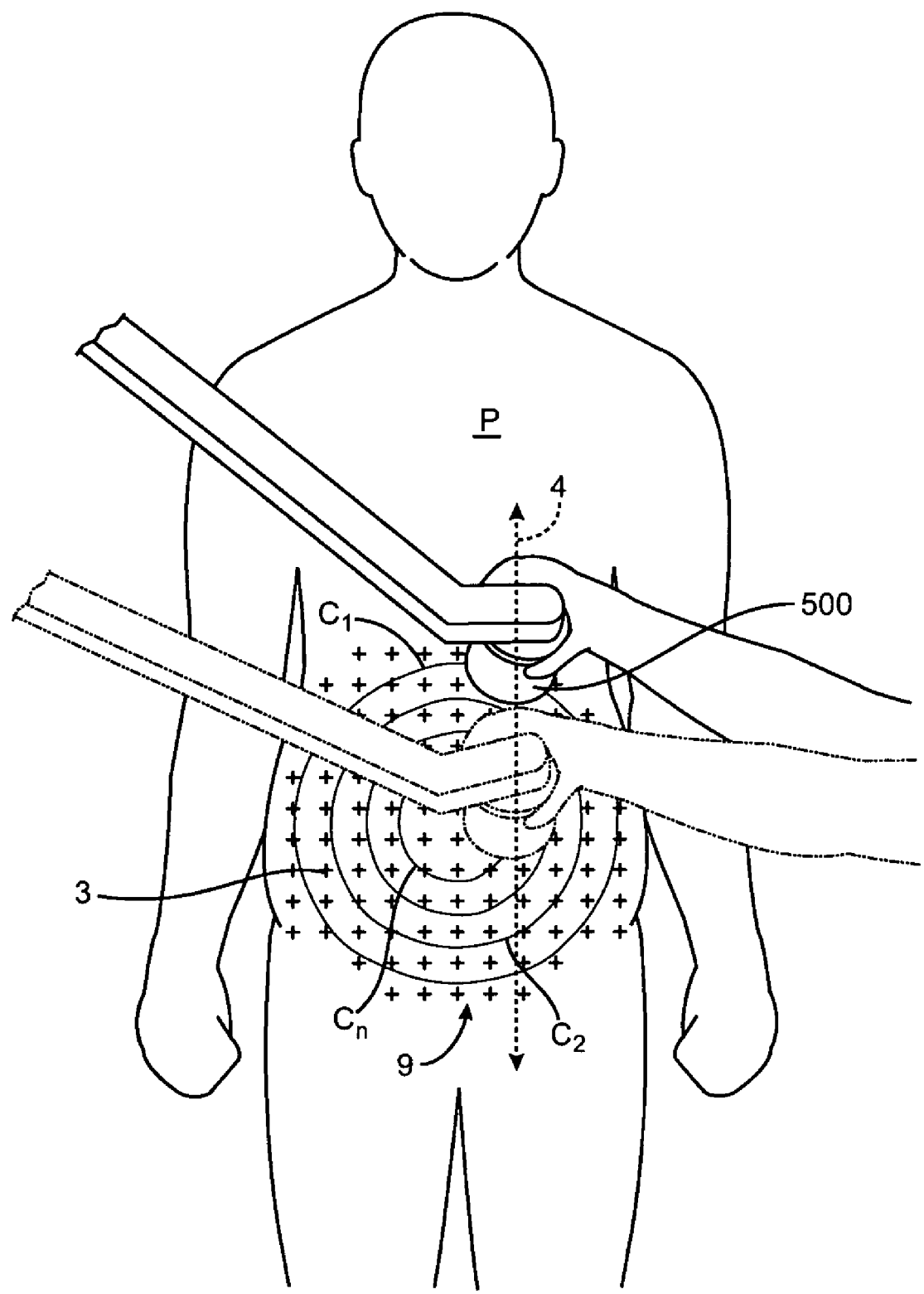
FIG. 2 illustrates the motion of a HIFU treatment device over the patient.
Figure 10:
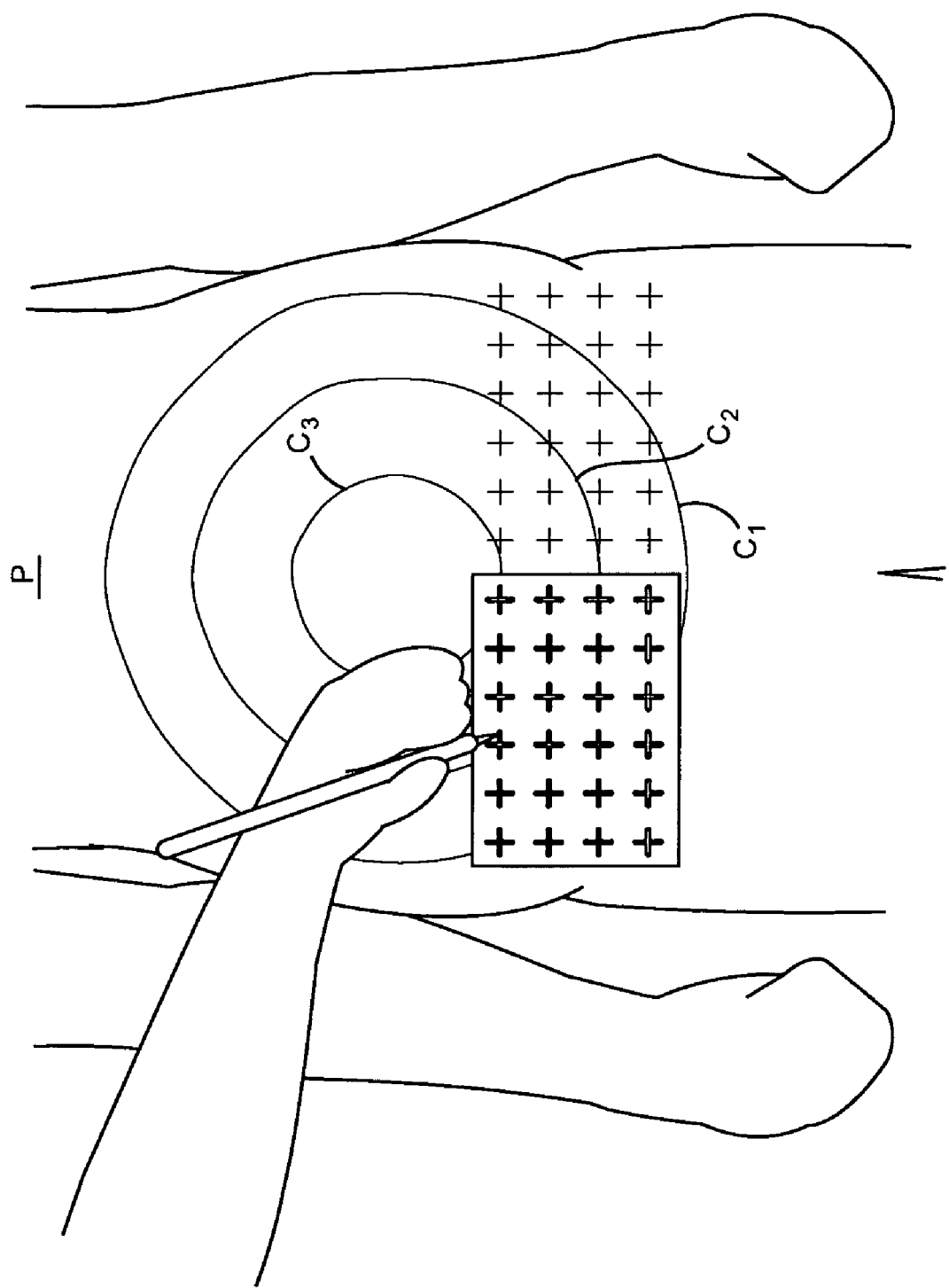
FIG. 10 illustrates the use of a stencil on a patient.

The stencil 24 can be laid across the patient (FIG. 10) and then the crosshairs drawn in using a medical marker. The combination of crosshairs and contour lines shown in FIG. 1 combine to provide visual markers for the safe placement of a HIFU transducer in an ordered fashion (using the guide marks) within a known depth of adipose tissue (using the contour lines). Once the two markings are on the patient, the physician need only line up the ultrasound treatment device with the crosshairs and contour lines (FIG. 2) to produce a mosaic of treatment sites 2 (FIG. 11).

The volume of tissue to be treated can be done using techniques already adopted by physicians in the ordinary practice of procedures like UAL. The physician can use a manual pinch test, calipers or diagnostic ultrasound to determine the depth of the fat tissue to be treated and draw circles around the region to be treated, similar to relief lines on a topographical map. The individual marks from the stencil may be made before the volume is determined, or after. The contour lines representing varying levels of tissue volume, and therapy head land marks overlap to provide the user with a defined safe area to treat, as well as a guide for treatment using the ultrasound therapy head.

Figure 13:
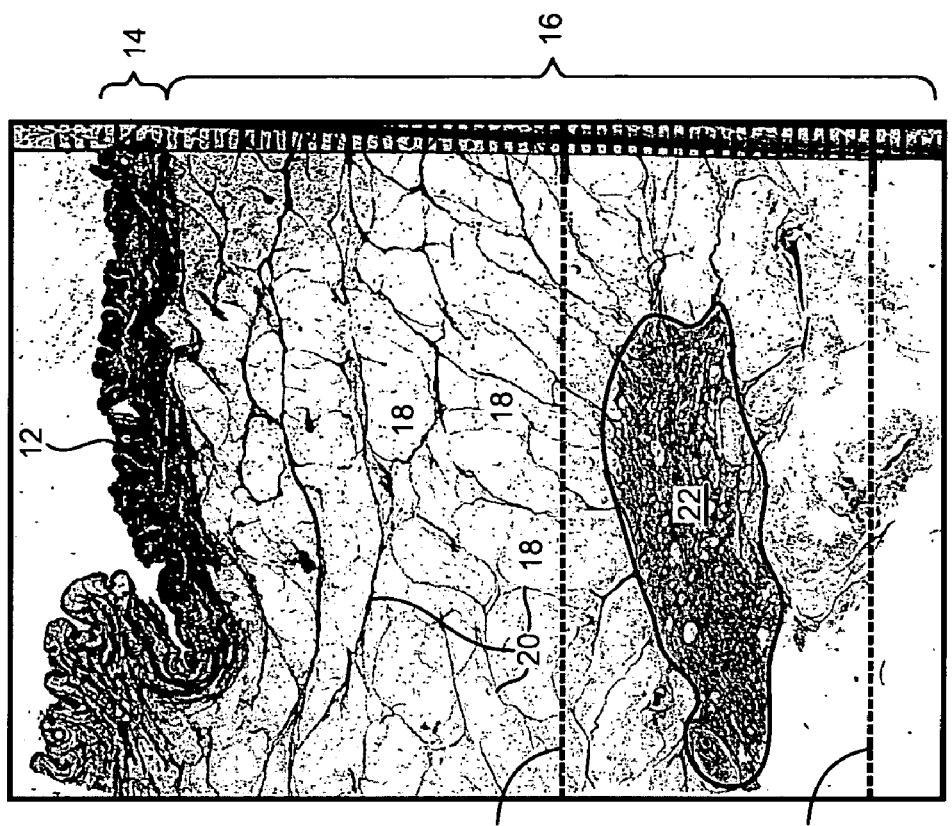
FIGS. 12-13 show histology slides of actual treated tissue.
Figure 12:
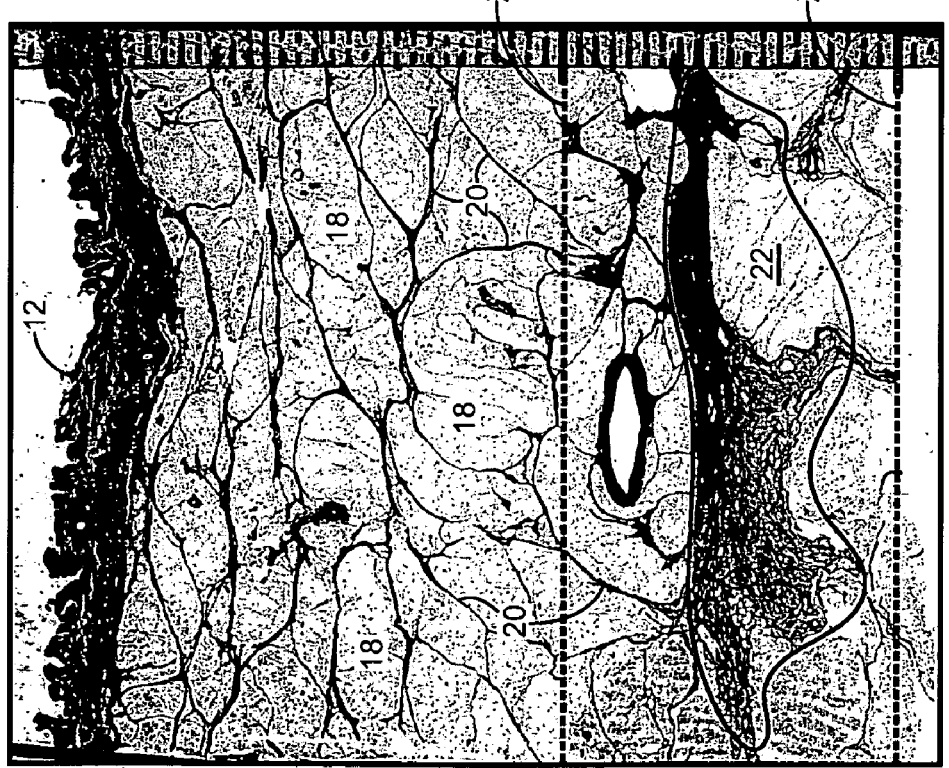

Proper utilization of the methods described herein can reduce the volume of a region of adipose tissue. Histology slides of tissue using the methods described herein are shown in FIGS. 12 and 13. These histology pictures show both the skin line 12 and skin layer 14 are undamaged. There is also shown a region of adipose tissue 16 having a relatively safe depth for this type of treatment. The treatment zone is found between the markers Z1 and Z2. Normal adipocytes (fat cells) 18 and normal collagen fibrils 20 are shown between the skin layer 14 and the treatment zone Z1. Within the treatment lines Z1, Z2 are shown two regions of heavy collagen population and nearly complete lack of adipocyte structures. The lesion field 22 shows both the collapse and destruction of adipose tissue and the denaturing of collagen fibrils which contract the tissue volume as the destroyed tissue mass is gradually removed from the body (through the body's natural wound healing response). The reduction of adipose tissue volume in this manner provides a similar long term result to liposuction. Since the tissue loss is gradual, there is no sudden looseness of the skin layer, nor skin deformation observed immediately after a patient undergoes a treatment using the methods described herein.

Review of the material disclosed herein will provide one skilled in the art with numerous alternative methods of accomplishing the desired objectives described, as well as methods not specifically mentioned herein. The description provided should be taken as illustrative and non-limiting, thus the present embodiments as well as alternative embodiments and equivalents are intended to be captured by the accompanying claims.

What is claimed is:

1. A method of modifying adipose tissue in a patient using high intensity focused ultrasound, the method comprising the steps of:
   determining a volume of adipose tissue to be treated;
   identifying a corresponding surface area of skin over said volume of adipose tissue;
   marking the patient's skin to create a plurality of guide markers at a predetermined spacing on the patient's skin within the surface area;
   moving a HIFU therapy transducer successively from guide marker to guide marker on said surface area of skin; and
   applying therapeutic ultrasound energy into said volume of adipose tissue at a power and for a time at each of said guide markers, wherein the power and time of applying said energy and the spacing of said guide markers are selected such that a plurality of necrosed tissue cells and denatured collagen fibrils are produced within a plurality of adjacent treatment cells covering substantially all of the treatment volume.

2. The method as described in claim 1, wherein moving the HIFU therapy transducer is performed in a raster scan pattern.

3. The method as described in claim 1, wherein the plurality of cells form a contiguous lesion field.

4. The method as described in claim 1, wherein the moving the transducer is done in a continuous motion.

5. The method as described in claim 1, wherein the moving the transducer is done in a discontinuous motion.

6. The method as described in claim 1 wherein moving the HIFU transducer is done while applying therapeutic ultrasound energy.

7. The method as described in claim 1, wherein moving the HIFU transducer is done when the transducer is not applying ultrasound energy.

8. The method as described in claim 1, wherein the applying of therapeutic ultrasound energy raises the temperature of the focal zone to at least 46° C.

9. The method as described in claim 1, wherein the applying of therapeutic ultrasound energy raises the temperature of the adipose tissue to at least 56° C. for at least one second.

10. The method of claim 1, wherein the thermal energy may be measured as an energy flux (EF) and determined by the relationship:

$$[(p) \times (l/v) \times (dc) \times (nl)]/(sa)$$

wherein
p=power,
l=line length,
v=velocity,
dc=duty cycle,
nl=number of lines
and
sa=scanned area.

11. The method of claim 10, wherein the energy flux is between 35 J/cm$^2$ and 460 J/cm$^2$.

* * * * *